United States Patent [19]

Logan et al.

[11] 4,210,594

[45] Jul. 1, 1980

[54] PROCESS FOR SEPARATING ESTERS OF FATTY ACIDS

[75] Inventors: Ted J. Logan; David C. Underwood, both of Cincinnati, Ohio

[73] Assignee: The Procter & Gamble Company, Cincinnati, Ohio

[21] Appl. No.: 24,759

[22] Filed: Mar. 28, 1979

Related U.S. Application Data

[63] Continuation of Ser. No. 858,484, Dec. 8, 1977, abandoned.

[51] Int. Cl.$^2$ ............................. C09F 5/10; C11B 3/00
[52] U.S. Cl. ................................ 260/428.5; 260/428; 260/419; 260/412.8
[58] Field of Search ...................... 260/412.8, 419, 428, 260/428.5

[56] References Cited

U.S. PATENT DOCUMENTS

| | | | |
|---|---|---|---|
| 3,269,750 | 8/1966 | Peck et al. ........................... | 260/666 |
| 3,510,423 | 5/1970 | Neuzil et al. ........................ | 208/310 |
| 4,048,205 | 9/1977 | Neuzil et al. ........................ | 260/428 |
| 4,049,688 | 9/1977 | Neuzil et al. ........................ | 260/428 |

OTHER PUBLICATIONS

Lopez-Ruiz et al., Grasas y Aceites 22(5) pp. 351-357 (1971); 23(4) pp. 285-291 (1972); 25(5) pp. 280-284 (1974).
Lopez-Ruiz, Doctoral Thesis "Molecular Slevis in the Chemistry of Fats" (1973).
DeVries B., J.A.O.C.S., vol. 40, pp. 184-186 (1963).
Subbaram M., J.A.O.C.S., vol. 41, pp. 150-153 (1964).
Kuemmel et al., Anal. Chem., vol. 38, No. 11, pp. 1611-1614 (1966).
Anderson et al., J. Lip. Res., vol. 6, No. 4, PP 577-578 (1965).

*Primary Examiner*—John F. Niebling
*Attorney, Agent, or Firm*—Ronald L. Hemingway; Richard C. Witte

[57] ABSTRACT

Continuous, countercurrent flow, fluid-solid contacting process for the separation of more unsaturated fatty acid ester from a less unsaturated fatty acid ester in a mixture comprising the two types of esters. The solid adsorbent utilized in said process is a Type X or Type Y zeolite containing specified cations at the exchangeable cationic sites, and the desorbent is a mixture of a paraffinic hydrocarbon and an ether.

38 Claims, 1 Drawing Figure

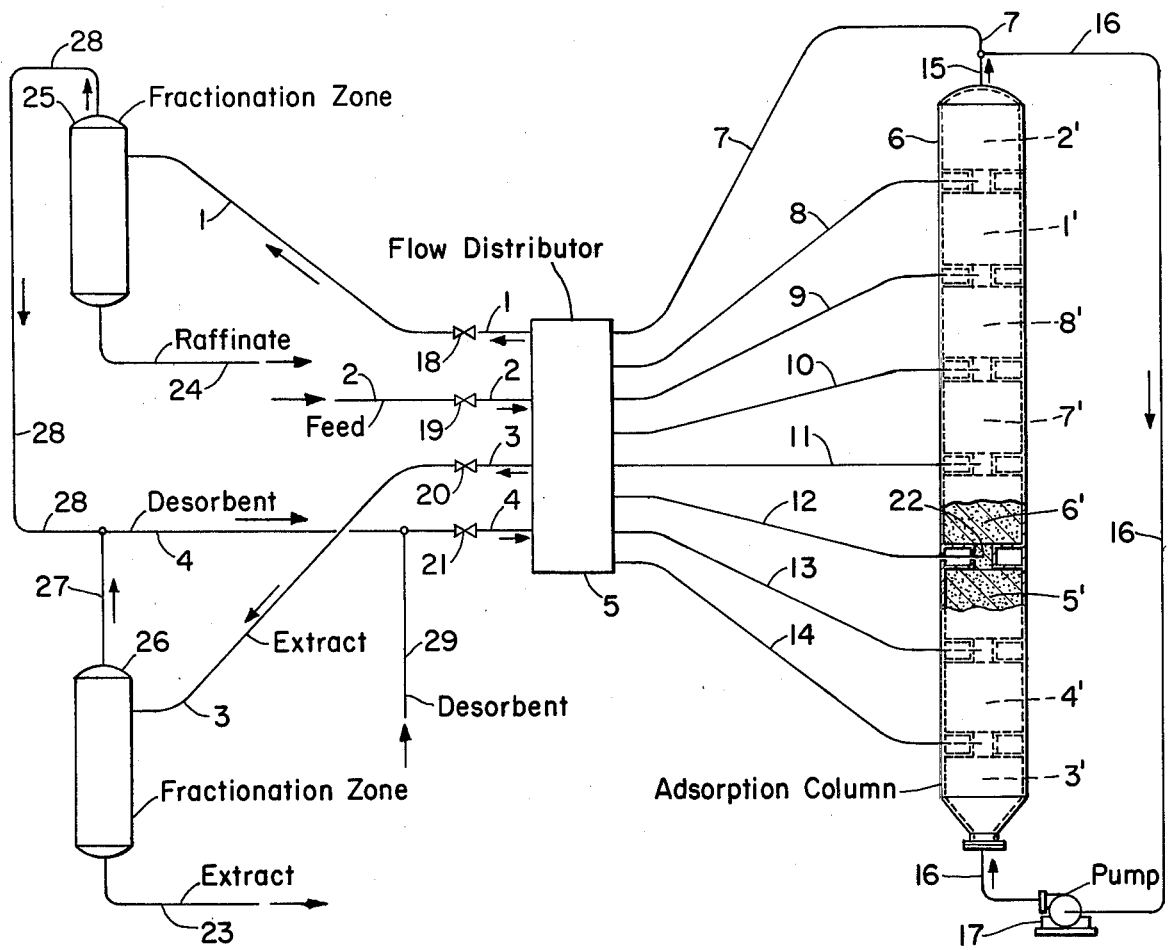

PROCESS FOR SEPARATING ESTERS OF FATTY ACIDS

This is a continuation, application Ser. No. 858,484, filed Dec. 8, 1977 now abandoned.

BACKGROUND OF THE INVENTION

The field to which this invention pertains is the separation of fatty acid esters by degree of unsaturation. More specifically the invention relates to a continuous process for separating esters of more unsaturated fatty acids from esters of less unsaturated fatty acids in a mixture comprising the two types of esters, by contacting said mixture with a solid zeolite adsorbent which has a higher affinity for more unsaturated fatty acid esters, and then desorbing the adsorbed esters from the adsorbent.

It is often important to separate fatty materials such as fatty acid esters into fractions of different degrees of unsaturation since there are specific uses for fatty materials having, respectively, higher or lower degrees of unsaturation. This is especially true in the manufacture of drying oils for coatings, the manufacture of resins and plasticizers, the compounding of cosmetic products and in the manufacture of chemical derivatives. For such purposes, a fatty acid ester product becomes more valuable as the proportion of the desired (i.e., more unsaturated or less unsaturated components) is increased in the product.

The zeolites used as the adsorbents herein have a preferential affinity for the more unsaturated components of a fatty acid ester mixture, i.e., the higher the degree of unsaturation, the higher the affinity. Accordingly, in the process of the invention, the fraction of the fatty acid ester feedstock which is adosrbed on the zeolite becomes enriched in the more unsaturated components, while the fraction which remains unadsorbed becomes enriched in the less unsaturated components.

The use of zeolite adsorbents (also called molecular sieves) to separate olefinic hydrocarbons from paraffinic hydrocarbons is well known. For example, U.S. Pat. No. 3,265,750 issued Aug. 9, 1966, to Peck et al., and 3,510,423, issued May 5, 1970, to Neuzil et al., describe the use of X and Y zeolites to conduct such separations.

DESCRIPTION OF THE INVENTION

It is the broad object of the invention to provide a continuous process for separating more unsaturated fatty acid esters from less unsaturated fatty acid esters in a mixture comprising fatty acid esters of different degrees of unsaturation. In a more specific sense it is an object of the invention to provide a continuous process for conducting the above separation utilizing zeolite molecular sieves as adsorbents for selectively adsorbing the more unsaturated esters from a mixture comprising more unsaturated and less unsaturated esters, and utilizing a safe and effective desorbent solvent system for desorbing the adsorbed esters from the adsorbent.

In its broadest aspect, the present invention comprises a continuous process for separating an ester of a more unsaturated fatty acid from a mixture comprising an ester of a more unsaturated fatty acid and an ester of a less unsaturated fatty acid, which process comprises the steps of (a) contacting said mixture in the fluid state, with a solid adsorbent, thereby selectively adsorbing said ester of a more unsaturated fatty acid; (b) removing from the adsorbent a raffinate stream enriched (relative to the composition of the original mixture) in said ester of a less unsaturated fatty acid; (c) contacting said adsorbent with a fluid desorbent material to effect desorption of said ester of a more unsaturated fatty acid from said solid adsorbent; and (d) removing from said solid adsorbent an extract stream enriched (relative to the composition of the original mixture) in said ester of a more unsaturated fatty acid; wherein said adsorbent comprises an X or Y zeolite containing at cation exchangeable sites at least one cation selected from the group consisting of metals of Group IA of the Periodic Table of Elements, magnesium, calcium, strontium, barium, silver, gold, zinc, nickel, copper, cadmium and mercury and combinations thereof; wherein said fluid desorbent material consists essentially of a mixture of one or more paraffinic hydrocarbons containing from about 5 to about 12 carbon atoms, and one or more ethers having the formula

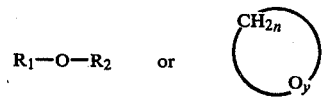

$$R_1-O-R_2 \quad \text{or}$$

wherein $R_1$ and $R_2$ are alkyl groups containing from about 2 to about 6 carbon atoms, n is 4 or 5, y is 1 or 2 and the sum of n and y is 5 or 6, wherein the volume ratio of paraffinic hydrocarbon to ether is from about 9:1 to 1:9, and wherein contact between solid adsorbent and fluids in said process is effected by means of continuous countercurrent flow fluid-solid contact.

A preferred embodiment of the present invention is a continuous simulated moving-bed process for the separation of an ester of a more unsaturated fatty acid from a mixture comprising an ester of a more unsaturated fatty acid and an ester of a less unsaturated fatty acid, which process comprises the steps of:

(a) introducing a feed stream of said mixture into a first zone in an adsorption column, which column effects overall fluid flow under substantially isothermal liquid phase conditions from a fourth zone through intervening serially connected third and second zones to a first zone, which column contains at least four serially-connected fixed-beds of an adsorbent, and adsorbing in said first zone at least a portion of said esters of said more unsaturated and less unsaturated fatty acids within the pores of said adsorbent;

(b) in said second zone, located immediately upstream of said first zone, contacting said adsorbent, containing said esters of said more unsaturated and less unsaturated fatty acids within the pores of said adsorbent, with a fluid desorbent material to effect displacement of said ester of a less unsaturated fatty acid from within the pores of said adsorbent;

(c) at the upstream boundary of said second zone, simultaneously withdrawing an extract stream comprising at least a portion of said ester of a more unsaturated fatty acid which has been previously desorbed in said third zone immediately upstream of said second zone;

(d) simultaneously introducing into said third zone, a desorbent material stream to effect said desorption;

(e) at the upstream boundary of said fourth zone located immediately upstream of said third zone and in open fluid communication with said first and said third zones, simultaneously withdrawing a relatively less selectively adsorbed raffinate stream comprising at least a portion of said ester of a less unsaturated fatty acid; and (f) periodically and simultaneously advancing the points of introduction of said feed stream and said desorbent material, and the points of withdrawal of said extract stream and said raffinate stream, one bed length in a downstream direction;

wherein in said process the adsorbent comprises an X or a Y zeolite containing at exchangeable cationic sites at least one cation selected from the group consisting of cations of metals of Group IA of the Periodic Table of Elements, magnesium, calcium, strontium, barium, silver, gold, zinc, nickel, copper, cadmium and mercury, and combinations thereof, and wherein said desorbent material consists essentially of a mixture of one or more paraffinic hydrocarbons containing from about 5 to about 12 carbon atoms, and one or more ethers having the formula

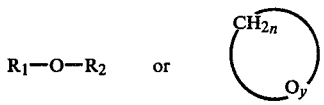

wherein $R_1$ and $R_2$ are alkyl groups containing from about 2 to about 6 carbon atoms, n is 4 or 5, y is 1 or 2 and the sum of n and y is 5 or 6, and wherein the volume ratio of paraffinic hydrocarbon to ether is from about 1:9 to 9:1.

The present process can be used to separate unsaturated fatty acid esters from each other according to their degree of unsaturation (e.g., monounsaturate from diunsaturate). It can also be used to separate an ester of an unsaturated fatty acid from a mixture comprising an ester of an unsaturated fatty acid and an ester of a saturated fatty acid, in which case the ester of the saturated fatty acid is considered to be "an ester of a less unsaturated fatty acid." For example, the process can be used to separate methyl oleate, methyl linoleate or methyl linolenate or all three, from methyl stearate, or methyl palmitate or both. Likewise, the process can be used to separate, for example, methyl oleate from methyl linoleate or methyl linolenate or both.

The use of X and Y zeolites to effect separations between more and less unsaturated fatty acid esters is described in the copending application of Logan, Ser. No. 846,300, filed Oct. 28, 1977, now abandoned, and incorporated by reference herein. The present invention is directed specifically to the carrying out of such separations in a continuous manner utilizing countercurrent flow fluid-solid contact.

The Feedstock

The fatty acid esters which comprise the feedstock which is to be separated according to the present process are reaction products of a fatty acid and a saturated lower ($C_1$-$C_4$) alkyl alcohol. Generally, the alcohol is a monohydric short chain alcohol such as methanol, ethanol, propanol, isopropanol or butanol. From a commercial standpoint the methyl esters are especially important and for purposes of simplicity the present process will be described primarily with reference to methyl esters, although it should be kept in mind that other lower alkyl esters of fatty acids can also be separated by the process.

The fatty acids from which the esters are made comprise a large group of monocarboxylic aliphatic acids which can be saturated (i.e., no double bonds) or unsaturated (i.e., containing one or more double bonds). The most common of these acids contain from about 6 to about 22 carbon atoms in the aliphatic chain and 0, 1, 2 or 3 sites of double bond unsaturation. Thus, an ester containing no double bonds in the fatty acid moiety is the least unsaturated, and one containing 3 double bonds in the fatty acid moiety is the most unsaturated. The present process includes the separation of an ester of an unsaturated fatty acid, from an ester of a saturated fatty acid, in which case, of course, the ester of the saturated fatty acid is considered to be the ester of a less unsaturated fatty acid, and the ester of the unsaturated fatty acid is considered to be the ester of a more unsaturated fatty acid.

Examples of individual esters are methyl stearate, methyl caprate, methyl laurate, methyl palmitate, methyl lauroleate, methyl myristoleate, methyl oleate, methyl eicosanate, methyl linoleate, methyl linolenate, methyl eleostearate and methyl elaidate. Methyl esters of fatty acids are normally produced commercially by methanolysis of naturally occurring glycerides, rather than by reaction with fatty acids per se. The fatty chains within these glycerides vary within the same glyceride molecule, as well as between glyceride molecules, in chain length and in degree of unsaturation; thus the methyl esters so produced are also mixtures. For example, typical mixtures of methyl esters obtained from the methanolysis, respectively, of soybean oil and beef tallow, have the following compositions:

TABLE I

| Composition of Fatty Methyl Esters (% by Weight) | | |
|---|---|---|
| | From Soybean Oil | From Tallow |
| Saturates | | |
| Myristate or lower | Tr.–0.5 | 2–8 |
| Palmitate | 7–11 | 24–37 |
| Stearate | 2–6 | 14–29 |
| Eicosanate or higher | 0.3–3 | Tr.–1.2 |
| Unsaturates | | |
| Palmitoleate or lower | Tr.–1 | 2.3–3.3 |
| Oleate | 15–33 | 40–50 |
| Linoleate | 43–56 | 1–5 |
| Linolenate | 5–11 | — |

The fatty acid esters used as feedstock in the present process generally contain from 7 to about 26 carbon atoms per molecule.

In most cases, feed mixtures which are charged to the present process then will be those comprising an ester of an unsaturated fatty acid and an ester of a saturated fatty acid, with the object of the process being to separate the mixture into saturates and unsaturates. Preferred as feedstocks for the present process are methyl esters of such fatty acids. The feed mixtures will typically contain one or more unsaturated fatty acid esters, which may be monoethenoid, diethenoid, triethenoid, etc., or mixtures thereof, and one or more saturated fatty acid esters. An example of a feed mixture is one containing: 1 wt. % $C_{14}$ and lower saturated compounds; 28 wt. % methyl palmitate; 19 wt. % methyl stearate; 42 wt. % methyl oleate; 9 wt. % methyl linoleate; and 1% methyl linolenate and higher saturates and unsaturates. Except for the small amount of $C_{14}$ and lower material and the small amount of linolenate and higher saturate and unsaturate material, such feed mixture consists essentially of $C_{16}$ and $C_{18}$ methyl esters of fatty acids and more specifically consists of two saturated fatty acid esters, one monoethenoid unsaturated fatty acid ester and one diethenoid unsaturated fatty acid ester. From a commercial standpoint, the esters which are most important for use in the present separation process are the esters (particularly methyl esters) of $C_{14}$ and $C_{20}$ fatty acids having 0, 1, 2 and 3 double bonds in the fatty acid chains.

Feed mixtures which can be charged to the present process may contain, in addition to fatty acid esters, a diluent material, that is not adsorbed by the adsorbent and which is preferably separable from the fatty acid esters which are separated by the process, e.g., by distillation. Paraffinic hydrocarbons are examples of suitable diluents. Normal hexane, 2,2,4-trimethyl pentane and normal octane are specific examples of paraffinic hydrocarbons that can be used as diluents, and can easily be distilled from the fatty acid esters. When a diluent is employed the concentration of diluent in the mixture of diluent and fatty acid esters will generally be from about 2% to about 90% by weight, with the remainder being fatty acid esters.

The Adsorbents

The adsorbents which are used in the process of the present invention are the crystalline aluminosilicates designated as X and Y zeolites. They are also referred to in the art as X and Y molecular sieves. These materials are well known and have been described, respectively, in U.S. Pat. Nos. 2,882,244, Milton, issued Apr. 14, 1959, and 3,130,007, Breck, issued Apr. 21, 1964, both incorporated herein by reference. Zeolite X has the formula:

$$(0.9 \pm 0.2)M_{\frac{2}{n}}O:Al_2O_3:(2.5 \pm 0.5)SiO_2:xH_2O$$

wherein "M" represents a metal cation, "n" is its valence and "x" may be any value up to 8, depending on the identity of the metal and the degree of hydration of the crystal.

Zeolite Y has the formula:

$$(0.9 \pm 0.2)M_{\frac{2}{n}}O:Al_2O_3:wSiO_2:xH_2O$$

wherein "M" represents a metal cation, "n" is its valence, "w" is a value greater than 3 up to about 6 and "x" may be a value up to about 9, depending on the identity of M, and the degree of hydration of the crystal.

The position of "M" in the zeolite crystalline structure is normally referred to as an exchangeable cationic site.

Zeolites X and Y are normally produced and sold in the sodium form, i.e., "M" in the above formulas is sodium. If it is desired to substitute other metal ions for sodium at the exchangeable cationic sites, this can be accomplished by conventional cation exchange techniques, e.g., treating the sodium sieve with an aqueous solution of a salt of the desired cation.

The X and Y zeolites for use in the process of the present invention can have any of the following metals at the exchangeable cationic sites: the metals of Group IA of the Periodic Table of Elements (e.g., lithium or sodium), magnesium, calcium, strontium, barium, silver, gold, zinc, copper, cadmium, mercury and nickel, or combinations thereof. The Group IA metals, especially sodium, are preferred.

The zeolites, as produced and sold commercially, normally contain, in addition to the actual zeolite, an inert diluent such as clay. Typical commercial material contains about 20% by weight clay and about 80% by weight zeolite. The zeolites are available commercially from The Linde Company, Tonawanda, New York.

It is generally preferred that the zeolite adsorbent used in the process herein have a water content of 0% to about 10% by weight of the zeolite. A given moisture level can be achieved by heating the zeolite in a oven to constant weight to drive off all water, and then rehydrating the zeolite with the desired amount of water. The adsorbent used in the present process can have a particle size range of from about 20 to about 80 mesh (Standard U.S. Mesh) and will preferably have a particle size within the range of about 20 to 40 mesh.

The X and Y zeolites herein have a high affinity for the double bonds in the unsaturated esters, therefore, the feed material, upon contact with the zeolite, becomes separated into a raffinate, enriched in the less unsaturated components, and an extract (on the adsorbent) enriched in the more unsaturated components. Degree of separation obtained can be determined by analysis of the raffinate and extract streams, using standard gas-liquid chromatographic techniques. If further enrichment of either stream is desired beyond that which can be obtained in one run through the process, the respective streams can be recycled as feed streams to the process. Thus, for example, one run of a feedstock through the process can be used to separate saturates from unsaturates, and then the extract stream, substantially free of saturates, can be passed through the process again to separate the unsaturated esters from each other by degree of unsaturation.

The ability of an adsorbent to preferentially adsorb one material over another in a mixture of materials in contact with the adsorbent can be expressed as relative selectivity. The relative selectivity can be expressed not only for one feed component as compared to another but can also be expressed between any feed mixture component and the desorbent material. The selectivity, (B), as used throughout this specification is defined as the ratio of the two components of the adsorbed phase over the ratio of the same two components in the unadsorbed phase at equilibrium conditions. The mathematical expression of relative selectivity is shown in the following equation:

$$\text{Selectivity} = (B) = \frac{[\text{Concentration } M/\text{Concentration } N]_A}{[\text{Concentration } M/\text{Concentration } N]_U}$$

where M and N are two components of the feed represented in volume or weight percent and the subscripts A and U represent the adsorbed and unadsorbed phases respectively. The equilibrium conditions are determined when the feed in contact with the adsorbent does not change composition with additional time in contact with the adsorbent. In other words, there is no net transfer of material occurring between the unadsorbed and adsorbed phases. Where the selectivity (B) between two components is 1.0 there is no preferential adsorption of one component by the adsorbent with respect to the other. A selectivity (B) of less than or greater than 1.0 indicates there is a preferential adsorption of the adsorbent for one component with respect to the other. A relative selectivity (B) of larger than 1.0 for one component M over another component N, indicates that M is preferentially adsorbed, thus the extract phase (on the adsorbent) is enriched in M, and the raffinate phase (i.e., the unadsorbed phase) is enriched in N. The higher the relative selectivity of an adsorbent for an extract component over a raffinate component, the easier the separation is to perform. Generally, (B) values of 2 or greater for an extract component over a raffinate component are preferred.

A dynamic fluid chromatography testing apparatus is employed to determine the selectivity of the zeolite adsorbent for fatty acid esters of different degrees of unsaturation in the presence of a desorbent, and thereby predict the ability of the system to perform in a continuous countercurrent flow fluid-solid contact process. The apparatus consists of an adsorbent column of 120 cm length and 7 mm inside diameter, having inlet and outlet ports at opposite ends of the column. The column is in a temperature controlled environment. A constant flow pump is used to pump the desorbent-feed mixture through the column at a predetermined flow rate. Quantitative and qualitative analytical equipment such as refractive index or U.V. detectors can be attached to the outlet port of the column and used to detect the components as they elute from the column. A dynamic test, performed using the above apparatus and the following general procedure, is used to determine selectivities and any other needed data for various adsorbent-desorbent combinations. The adsorbent is allowed to come to equilibrium with a particular desorbent material by passing the desorbent through the adsorbent column for a given period of time. As the desorbent is passing through the column, and at a convenient time, a pulse of feed containing a known amount of a tracer, and in a compatible medium (e.g., paraffinic hydrocarbon diluent), is injected, via a sample loop, into the system. The desorbent flow is essentially undisturbed during this operation. The pulse of feed plus tracer is allowed to flow through the column and separate into individual components as these components come into contact with the adsorbent, and in turn are desorbed by the desorbent. The effluent can be analyzed on stream or samples can be collected periodically and analyzed separately by analytical equipment. Graphs of the components can be plotted to show when and where they eluted off the column. The operation of such a dynamic test is illustrated in Example I of this specification.

From information derived from the test adsorbent, performance can be rated in terms of void volume of the adsorbent, retention volume for an extract or a raffinate component, selectivity for one component with respect to the other, and the rate of desorption of an extract component by the desorbent. The retention volume of an extract or a raffinate component may be characterized by the distance between the peak of the elution curve of an extract or a raffinate component and the peak of the elution curve for the tracer component or alternatively some other known reference point (i.e., from time O). It is expressed in terms of the volume in cubic centimeters of desorbent pumped during this time interval represented by the distance between the peaks. Selectivity, (B), for an extract component with respect to a raffinate component may be characterized by the ratio of the distance between the extract component peak and the tracer peak (or other reference point) to the corresponding distance between the peak of the raffinate component and the peak of the tracer. The rate of exchange of an extract component with the desorbent can generally be characterized by the width of the peak envelopes at half intensity. The narrower the peak width the faster and desorption rate. The desorption rate can also be characterized by the distance between the tracer peak and the disappearance of an extract component which has just been desorbed. This distance is again the volume of desorbent pumped during this time interval.

The Desorbent

The selection of a proper desorbent solvent is essential to the effective operation of a continuous countercurrent flow fluid-solid contacting process as employed in the present invention and described in more detail below. By contrast, when X or Y zeolites herein are used as adsorbents in a batch-type process for separating saturated and unsaturated fatty acid esters, the choice of solvent for desorbing the adsorbed ester from the adsorbent is not especially critical. In such process, after the feed has been brought into contact with the adsorbent, the raffinate (enriched in the less unsaturated ester) can be drawn off and the adsorbent can then be contacted with a solvent to desorb the extract (enriched in the more unsaturated ester) from the adsorbent. Generally, any solvent which is capable of dissolving the fatty acid esters and is compatible with the esters can be used as the desorbent in such a process. Preferably, it should be one which can be used in reasonably small quantities to desorb the adsorbed esters and will have a boiling point such that it can be separated from the esters by distillation. Examples of some of the solvents which can be used are ketones, such as acetone, ethers such as diethyl ether or diisopropyl ether, amides such as dimethyl formamide, olefins such as 1-hexene or 1-octene, esters such as methyl acetate, ethyl acetate or methyl propionate, and alcohols such as methanol and ethanol. Saturated hydrocarbons, although good solvents for fatty acid esters, are not good desorbents when used alone since large quantities are needed to desorb the fatty acid esters from the zeolite adsorbent. The saturated hydrocarbons can be combined with various of the solvents described above to produce effective desorbent systems.

With respect to a continuous countercurrent flow fluid-solid contacting process as employed herein, particularly one utilizing a simulated moving-bed technique, the desorbent (which is a solvent or mixture of solvents) must be one which does not unduly affect the selectivity of the adsorbent for the more unsaturated fatty acid esters over the less unsaturated fatty acid esters, since both types of esters and the desorbent are all simultaneously in contact with the adsorbent. The desorbent must also, of course, be chemically compatible with the esters and should have a boiling point which renders it easily separable from the esters by distillation. It should also be a material which is industrially suitable from the standpoint of cost, availability and industrial hygiene.

It has been found that a solvent system meeting these criteria for being a suitable desorbent material for the process of the invention is a mixture of a paraffinic hydrocarbon and an ether.

Suitable paraffinic hydrocarbons are those which contain from about 5 to about 12, preferably from about 5 to about 8 carbon atoms. They can be cyclic or acylic, straight chain or branch chain. Preferably they are acyclic and straight chain. Mixtures of paraffinic hydrocarbons can be used. Examples of suitable paraffinic hydrocarbons are isopentane, n-hexane, n-octane, 2-methyl octane, cyclohexane and methyl cyclohexane.

Suitable ethers are those having the formula $R_1—O—R_2$ wherein $R_1$ and $R_2$ are alkyl groups containing from about 2 to about 6 carbon atoms, and those having the formula

wherein n is 4 or 5, y is 1 or 2 and the sum of n and y is 5 or 6.

The "R" groups can be cyclic, or acyclic, straight chain or branched chain. The dialkyl ethers can be symmetrical or unsymmetrical, but are preferably symmetrical. The cyclic ethers can be 5 or 6 member rings, containing 1 or 2 oxygen atoms in the ring. Mixtures of ethers can be used. Examples of suitable ethers are ethyl propyl ether, diisopropyl ether, dibutyl ether, ethyl butyl ether, dihexyl ether, ethyl cyclohexyl ether, tetrahydrofuran, tetrahydropyran, 1,3-dioxane and 1,4-dioxane.

The volume ratio of paraffinic hydrocarbon to ether in the desorbent should be from about 1:9 to about 9:1, preferably from about 2:1 to about 1:2, and most preferably about 1:1. Preferred desorbent solvent systems are those consisting essentially of diisopropyl ether and n-hexane.

Process Description

Continuous countercurrent flow fluid-solid contacting processes for selective adsorption and/or removal of components from a feed stream by selective adsorption are well known in the art and the present process can be practiced by utilizing the hereindescribed feed mixtures, adsorbent and desorbent, in the apparatus and process steps of such processes. Examples of such processes are those described in the following U.S. Pat. Nos., which are incorporated by reference herein: 2,967,148, issued Jan. 3, 1961, to Karnofsky; 2,731,149, issued Jan. 17, 1956, to Findlay; 2,985,589, issued May 23, 1961, to Broughton et al.; and 3,510,423, issued May 5, 1970, to Neuzil et al.

The first two of these cited patents provide examples of continuous moving-bed countercurrent flow fluid-solid contacting processes. The latter two patents are simulated moving-bed countercurrent flow fluid-solid contacting processes, which is the preferred type of continuous process means for carrying out the present process.

A particularly preferred manner of practicing the present process is by the continuous simulated moving-bed countercurrent flow technique disclosed in U.S. Pat. No. 3,510,423, and the present invention will be illustrated by reference to that patent.

This embodiment of the present process may be understood more clearly by referring to the attached FIGURE. In describing the process a feedstock comprising unsaturated fatty acid esters (UE's) and saturated fatty acid esters (SE's) will be used. This could be, for example, a mixture of methyl palmitate, methyl stearate, methyl oleate and methyl linoleate. Adsorption column 6 in the figure, contains an X or Y zeolite adsorbent, as hereinbefore defined. Lines 1, 2, 3 and 4 are connected to flow distributor 5 and have flow controlling valves 18, 19, 20 and 21 attached for independent control of the individual raffinate, feed, extract and desorbent flow rates. Line 2 carries the feed to the flow distributor and subsequently to adsorption column 6. The feed flowing through line 2 into the flow distributor comprises SE's and UE's.

Line 1 of the attached figure carries the relatively less adsorbed components of the feed which comprises the SE's. This less selectively adsorbed component of the feed (raffinate material) flows through line 7 from column 6 at a rate which is controlled by valve 18. The raffinate material flowing from column 6, in addition to SE's comprises desorbent material (i.e., paraffinic hydrocarbon and ether as hereinbefore defined) which was displaced from the adsorbent by the UE's in the feed. The raffinate material flowing from column 6 is separated by fractionation zone 25 to yield desorbent and SE fractions, the desorbent is recycled to line 4 via line 28 for reuse and the SE is collected as product from line 24.

Line 3 of the attached figure carries extract material from column 6 at a rate controlled by valve 20. The extract material comprises feed-UE's and desorbent material and is a resultant stream formed by displacement of adsorbed feed UE's by the desorbent stream flowing through line 4. The extract stream flowing through line 3 is separated into a UE product stream and a desorbent stream in fractionation zone 26. The feed UE is recovered as product from line 23 and desorbent material is preferably recycled to line 4 via line 27 for reuse.

Line 4 of the attached figure carries desorbent material to adsorption column 6 at a rate controlled by valve 21. Line 29 is connected to line 4 and supplies desorbent from an external source as is needed.

Flow distributor 5 of the attached figure connects lines 1, 2, 3 and 4 to lines 7, 8, 9, 10, 11, 12, 13 and 14 which are connected to column 6. Lines 7 through 14 enter the column 6 through ports that are located between the eight individual fixed beds in a preferably narrow portion of the column 6. For example, line 12 enters the column 6 through port 22 between beds 5' and 6'. Flow distributor 5 can comprise a multi-valve manifold arrangement, a rotary multiport valve or any other suitable flow directing mechanism that will, in a programmed manner, direct flow of the feed (line 2) and desorbent (line 4) streams into the column and the raffinate (line 1) an extract (line 3) streams out of the column.

As shown in the attached figure, the feed flows through line 2 to flow distributor 5 wherein the feed is sent through line 9 to column 6; the desorbent flows through line 4 to the flow distributor which sends the desorbent through line 13 to the column; the raffinate stream flows from column 6 through line 7 to the flow distributor wherein the raffinate stream is sent through line 1 to fractionation facilities 25; the extract stream flows from the column through line 11 to the flow distributor which sends the extract stream through line 3 to fractionation facilities 26. The streams flowing into and out of the process as described above comprise a single cycle (Cycle 1 of Table II) of an operation which will vary in length of time according to the feed composition, required product purity, adsorbent properties, etc. Determination of the appropriate cycle time length for the particular result desired is well within the skill of the art.

Table II below indicates the locations of the feed, raffinate, extract and desorbent streams during the individual cycles used in the continuous operation of column 6.

TABLE II
FLOW DISTRIBUTOR PROGRAMMED OPERATION

| Cycle | \multicolumn{8}{c}{Lines through which material is flowing (see attached figure)} |
|---|---|---|---|---|---|---|---|---|

| Cycle | 7 | 8 | 9 | 10 | 11 | 12 | 13 | 14 |
|---|---|---|---|---|---|---|---|---|
| 1 | R |   | F |   | E |   | D |   |
| 2 |   | F |   | E |   | D |   | R |
| 3 | F |   | E |   | D |   | R |   |
| 4 |   | E |   | D |   | R |   | F |
| 5 | E |   | D |   | R |   | F |   |
| 6 |   | D |   | R |   | F |   | E |
| 7 | D |   | R |   | F |   | E |   |
| 8* |   | R |   | F |   | E |   | D |

R - Raffinate stream;
D - Desorbent stream;
E - Extract stream;
F - Feed Stream.
*Cycle 8 is the last cycle in completing one sequence of operations. After cycle 8 is completed, cycle 1 is started.

As can be seen in Table II, the raffinate, feed, extract and desorbent streams that flow to column 6 are advanced equally in the same direction when advancing to the next cycle of operations. It should be understood four or more cycles may be used and that the number of cycles required for one complete sequence of operations depends on the number of individual inlet-outlet ports that the column contains.

As can be seen in Table II, there are only four of the total of eight lines entering the column 6 that are in use during a given cycle. For example, in cycle 1 of Table I, lines 7, 9, 11 and 13 are in use while lines 8, 10, 12 and 14 are not in use. The flow distributor 5 is constructed in a manner so that the lines not having material flowing through them during a given cycle, i.e. lines 8, 10, 12 and 14 of cycle 1, are plugged or blocked off at either or both the flow director or column ends, thereby stopping flow through these lines. In this manner of selected flow in and out of column 6 in predetermined cycles, a simulated countercurrent moving bed operation is effected in column 6.

The adsorption column 6 of the attached figure is a plurality of serially connected fixed beds having more adsorbing affinity for UE's than for corresponding SE's. The beds can be in individual serially connected columns, or can be stacked in a single column as shown in the attached figure. The term "column" therefore, is used in the broadest sense in the present specification and claims to include a single column containing a plurality of fixed beds of adsorbent; or a series of serially connected individual columns, each containing one or more fixed beds of adsorbent. Column 6 contains eight fixed beds numbered 1' through 8' with the terminal beds (beds 2' and 3") connected by lines 15 and 16. Pump 17 in line 16 provides a means for circulating liquid from the top of column 6 to the bottom thereof. The pumparound system gives the fluid in column 6 a unidirectional flow which, relative to the stationary solid adsorbent, in the eight beds of column 6, flows from bed 3' to bed 2' via beds 4', 5', 6', 7', 8' and 1'. Relative to bed 3', bed 4' is in a downstream direction; relative to be 4', bed 3' is in an upstream direction by virtue of the direction of fluid flowing through the separate beds.

To reduce the operation of the adsorption column to relatively simplified terms, the column can be thought to be operating in continuous counterflow of liquid and said adsorbent with the overall separation of UE's and SE's being effected by four separate zones.

Zone I is the series of beds located between the port of feed introduction downstream to the port of raffinate withdrawal; zone II is the series of beds located between the port of extract withdrawal downstream to the port of feed introduction, zone III is the series of beds located between the port of desorbent introduction to the port of extract withdrawal; and zone IV is the series of beds located between the port of raffinate withdrawal downstream to the port of desorbent introduction. As mentioned previously, the ports of feed and desorbent introduction and the ports of raffinate and extract withdrawal are advanced equally and essentially simultaneously in a downstream direction (Table I). Consequently, zones I, II, III and IV are advanced equally and simultaneously in a downstream direction as the inlet and outlet ports are so advanced.

Table III shows the location of the individual zones throughout the series of beds in the adsorption column for the individual cycles used in the continuous operation of the adsorption column

TABLE III
ZONE POSITIONS IN THE ADSORPTION COLUMN FOR VARIOUS CYCLES OF OPERATION

| Cycle* | 1 | 2 | 3 | 4 | 5 | 6 | 7 | 8 |
|---|---|---|---|---|---|---|---|---|
| Adsorbent bed in column: | | | | | | | | |
| 1'. | I | II | II | III | III | IV | IV | I |
| 2'. | I | I | II | II | III | III | IV | IV |
| 3'. | IV | I | I | II | II | III | III | IV |
| 4'. | IV | IV | I | I | II | II | III | III |
| 5'. | III | IV | IV | I | I | II | II | III |
| 6'. | III | III | IV | IV | I | I | II | II |
| 7'. | II | III | III | IV | IV | I | I | II |
| 8'. | II | II | III | III | IV | IV | I | I |

*Cycles 1–8 are identical to the cycles of Table II.

In zone I, UE's in the feed are adsorbed by the solid adsorbent displacing the previously adsorbed desorbent. During the normal course of operation zone I is shifted as previously described. In using zone I as a reference point, when zone I shifts to the next bed position (Table III) the solids that leave zone I enter zone II. The adsorbent that is entering zone II carries UE's adsorbed from the feed and SE's from the feed. In zone II the SE's from the feed are displaced from the solid by desorbent and UE's. Any UE from the feed that is desorbed from the adsorbent in zone II is readsorbed in zone I. The adsorbent in zone III carries UE's from the feed and some desorbent and is contacted with a large excess of desorbent which displaces all of the UE's from the feed that were carried on the adsorbent. When zone III shifts to its new location in the adsorption column the adsorbent that leaves this zone carries primarily desorbent which can be made available for reuse in zone III by contacting the adsorbent with a portion of the raffinate. In zone IV the displacing of desorbent by raffinate material is accomplished. The raffinate flow rate into zone IV is controlled so that the raffinate material flowing into zone IV is completely adsorbed.

In starting the process, a feed stock comprising UE and SE mixture is charged into the process flow through line 2, at a rate controlled by valve 19, through flow director 5 and into line 9 which carries the feed into the column at the port located at the preferably narrow portion of the column located between beds 1' and 8'. The feed entering the column through the port of line 9 flows in a downstream direction into bed 1' wherein the UE's in the feed and some SE's are adsorbed by the solid adsorbent. Simultaneously, the desorbent present in the solid adsorbent pores from a previous cycle of operation is displaced from the adsorbent. The less strongly adsorbed SE's occupy the void spaces between the solid particles of the adsorbent and eventually flow downstream towards bed 2' and to line 7 which allows a portion of the raffinate stream (SE's and desorbent mixture) to be withdrawn from the column via line 7, the flow distributor 5 and line 1. The solid adsorbent in bed 1' contains, in addition to adsorbed UE's, a considerable quantity of SE's which can be displaced from the adsorbent by desorbent which, from a prior cycle, is contained in upstream beds 7' and 8'. The SE's which are displaced from the solid adsorbent in bed 1' by desorbent material flow in a downstream direction towards bed 2'. Unavoidably, some of the UE's adsorbed on the solid adsorbent in bed 1' are displaced at the same time. The flow rate of liquid flowing into bed 1' from bed 8' can be adjusted to displace substantially all of the SE's adsorbed by the adsorbent in beds 1' and 2', without simultaneously washing out all of the more tenaciously adsorbed UE's. Any UE's which are desorbed in bed 1' are readsorbed in bed 2'.

The SE material, together with desorbent material, are the principal materials withdrawn from bed 1', passing by the port of line 8 and entering bed 2' wherein any UE's in the material entering bed 2' can be adsorbed. The stream passing out of bed 2' through line 15 comprises principally the non-adsorbed SE's and desorbent. A portion of the fluid effluent from bed 2' in line 15 passes through line 7 to flow distributor 5 and through the raffinate line 1; the raffinate flow rate out of the column is controlled by valve 18 in line 1. The remaining portion of effluent from bed 2' flows through line 16 into bed 3'. Line 16 connects the terminal beds 2' and 3' and allows continuous unidirectional flow of liquid through the column.

The solid adsorbent in beds 3' and 4' contains within its pores essentially only adsorbed desorbent which is present from a previous cycle of operation. The raffinate material flowing through line 16 to bed 3' comprises primarily SE's which are adsorbed on the adsorbent in bed 3' displacing desorbent material downstream to bed 4' and bed 5'. The flow rate of the raffinate material into bed 3' is adjusted so that SE's are completely adsorbed on the adsorbent before reaching the outlet of bed 4'. Otherwise, the SE's would contaminate the UE product in the extract stream.

The solid adsorbent in beds 5' and 6' contains adsorbed UE's and desorbent from a previous cycle of operations. The adsorbed UE's, which have been selectively adsorbed from the feed, are displaced by desorbent material flowing through line 4, at a rate controlled by valve 21, to the flow distributor, through line 13 and out of the port of line 13 between beds 4' and 5'. The desorbent upon entering the column flows in a downstream direction into beds 5' and 6' displacing the UE product. The desorbent and UE material which comprises the extract stream flows out of column 6 at the port between beds 6' and 7' through line 11 to the flow distributor 5 and through line 3 at a rate controlled by valve 20 in line 3. A portion of the extract material flows past the port of line 11 into the next downstream bed 7'. Any UE product passing into bed 7' is adsorbed by the solid adsorbent in bed 7'. The desorbent material flowing through bed 7' into bed 8' tends to flush any adsorbed SE's that are carried within the solid when the feed line is shifted to line 8 (cycle 2).

Generally, the SE portion of the raffinate stream not withdrawn from column 6 through the raffinate withdrawal line does not contaminate the stream of liquid flowing beyond the first downstream bed from the port of raffinate withdrawal. The same conditions apply for the UE of the extract stream.

The above described flow of feed and desorbent streams into the column and extract and raffinate streams out of the column comprise cycle 1 of Table II; cycle 2 of Table II is then executed with the feed line switching from line 9 to 8, the raffinate line switching from line 7 to 14, the desorbent line switching from line 13 to 12, and the extract line switching from line 11 to 10. The lines are advanced in the direction of net liquid flow through the column in the valves 18, 19, 20 and 21 altering the input and output flow rates to achieve desired extract and raffinate purities.

Lines 7, 8, 9, 10, 11, 12, 13 and 14 carry different streams to and from the adsorption column during the individual cycles of operation of the flow distributor. To eliminate the contamination of raffinate and extract streams it is understood that a method of flushing the lines 7 and 14 is preferred. A preferred method of flushing the lines 7 through 14 is to pump desorbent material through the line immediately upstream of the feed inlet into the adsorption column as described in U.S. Pat. No. 3,201,491, Stine et al., issued Aug. 17, 1965, incorporated herein by reference. In flushing the line immediately upstream from the feed line, the extract which eventually will be flowing out of the desorption column through a previously flushed line will not be contaminated with the feed stock components not desired in the extract. This increases product (extract) purity and favorably affects the quality of the extract material.

Process Conditions

The continuous process of the present invention is generally carried out with the feed, desorbent, extract and raffinate streams all being in the liquid state at temperatures within the range of from about 25° C. to 300° C. (preferably from about 50° C. to 150° C.) and pressures within the range of from about atmospheric to 500 psig.

With respect to the simulated moving-bed embodiments of the process, it is preferred that the process be carried out under substantially isothermal conditions, meaning that difference in temperature through the entire series of adsorbent beds is less than about 10° C. Differences in pressure at various locations throughout the series of adsorbent beds provide the means of allowing liquid flow into, out of and through the series of adsorbent beds. Preferably, these differences in pressure should be less than about 50 psi., but can be as high as 200 psi.

Example I

This example, employing a dynamic test procedure, shows the determination of selectivities for more unsaturated fatty acid esters with respect to less unsaturated fatty acid esters which are obtained by utilizing the combination of adsorbent and desorbent of the present invention, thereby making possible the continuous separation process of the present invention. The adsorbent used in this representative example is Linde 13X molecular sieve. (Linde Company, Tonawanda, New York) This is a sodium X sieve consisting essentially of about 80% by weight zeolite molecular sieve and 20% by weight clay. The adsorbent used in the test was prepared by grinding the as-purchased adsorbent material and then screening to approximately 20-40 U.S. mesh particle size range. The adsorbent was then dried at 600° C. for approximately 16 hours, then allowed to cool under vacuum to room temperature before use. The room temperature adsorbent was treated with water to bring the water content to 5% by weight of the zeolite.

The feed mixture used was a mixture of methyl esters of fatty acids having the composition shown in Table IV.

TABLE IV

Experimental Feed Mixture Used

| | | Composition *(GLC % by Wt.) |
|---|---|---|
| $C_{14}$ | and Lower Saturates and Unsaturates | 1.0 |
| $C_{16}$ | Saturated (Methyl Palmitate) | 28.0 |
| $C_{18}$ | Saturated (Methyl Stearate) | 19.0 |
| $C_{18}^{1=}$ | One Double Bond (Methyl Oleate) | 42.0 |
| $C_{18}^{2=}$ | Two Double Bonds (Methyl Linoleate) | 9.0 |
| $C_{18}^{3=}$ | and Higher Saturates and Unsaturates | 1.0 |
| | | 100.0 |

*Composition determined by gas-liquid chromatography.

The dynamic test equipment and the general procedure have been previously described in this specification. The adsorbent was packed in a 120 cm ×7 mm inside diameter column maintained at 50° C. with a 50% by volume hexane, 50% by volumne diisopropyl ether mixture as desorbent. The column was first allowed to come to equilibrium with the desorbent at a flow rate of 2.0 mls per minute. A 1.0 ml portion of a solution prepared by diluting 24 grams of the above (Table IV) esters, and 2.4 grams of octacosane (used as a tracer material to establish the voia volume of the column), to 100 ml in hexane, was then injected into the upstream end of the column. The ester was allowed to migrate through the column at a 2.0 mls per minute flow rate. Fractions of the hexane-diisopropyl ether desorbent were collected at the downstream end of the column every 2.5 minutes over a period of 40 minutes starting at 5 minutes after injection and ending with the fraction taken at 40 minutes. The collected fractions were analyzed for ester and octacosane tracer content by GLC. The GLC results were plotted on graph paper versus time at which the fraction was collected. The plot showed the void volume of the column (as indicated by the position of the tracer curve) and the order in which the esters eluted. The retention volumes for the methyl esters were calculated by measuring the volumes from time zero (instant of injection) to the respective peaks of the methyl ester curves. Selectivities of each methyl ester were obtained by measuring the difference in retention volume from the peak of each methyl ester curve to the peak of the tracer curve, and by then dividing each of these differences by the retention volume difference of the $C_{16}$ saturated methyl ester. Therefore, by definition, the selectively of $C_{16}$ saturated methyl ester becomes 1.0. Results are shown in Table V.

TABLE V

Selectivity of Na-13X Zeolite Adsorbent for Unsaturated and Saturated Methyl Esters of Fatty Acid

| Test Material | Relative Retention Volume Difference | Selectivity |
|---|---|---|
| $C_{16}$ | 11 | 1.0 |
| $C_{18}$ | 8 | 0.7 |

TABLE V-continued

Selectivity of Na-13X Zeolite Adsorbent for Unsaturated and Saturated Methyl Esters of Fatty Acid

| Test Material | Relative Retention Volume Difference | Selectivity |
|---|---|---|
| $C_{18}^{1=}$ | 40 | 3.6 |

In this test the $C_{18}$ diunsaturated ester (methyl linoleate) did not elute from the column within 40 minutes at the 2 ml per minute flow rate, since the affinity of the adsorbent for methyl linoleate is higher than that for methyl oleate. To determine the selectivity of the adsorbent for methyl linoleate relative to the $C_{16}$ saturated ester (methyl palmitate) the test was repeated with a flow rate of 5 ml per minute. In this second test the relative retention volume difference between methyl palmitate and the tracer was found to be 4; and between methyl linoleate and the tracer was found to be 53. Therefore, the selectivity of the adsorbent for methyl linoleate over methyl palmitate is 53/4 or 13.3.

These results from the dynamic test illustrate the ability of sodium X zeolite adsorbent to preferentially adsorb more unsaturated fatty acid esters over less unsaturated fatty acid esters in the presence of a hexane-diisopropyl ether desorbent, thereby making a continuous process possible. Effective separations can also be obtained in a similar manner when the molecular sieve is sodium Y instead of sodium X. Likewise, separations can be obtained when the sodium ions have been exchanged for lithium, potassium, magnesium, calcium, strontium, barium, gold, nickel, zinc, cadmium, silver or mercury. Likewise, effective separation can be obtained when n-hexane in the desorbent is replaced by isopentane, n-octane, 2-methyl octane, cyclohexane and methyl cyclohexane, and when diisopropyl ether is replaced by ethyl propyl ether, dibutyl ether, ethyl butyl ether, dihexyl ether, ethyl cyclohexyl ether, tetrahydrofuran, tetrahydropyran, 1,3-dioxane or 1,4-dioxane.

What is claimed is:

1. A continuous process for separating an ester of a more unsaturated fatty acid from a feed mixture comprising an ester of a more unsaturated fatty acid and an ester of a less unsaturated fatty acid, which process comprises the steps of:
   (a) contacting said mixture in the fluid state, with a solid adsorbent, thereby selectively adsorbing said ester of a more unsaturated fatty acid;
   (b) removing from the adsorbent a raffinate stream enriched (relative to the composition of the original mixture) in said ester of a less unsaturated fatty acid;
   (c) contacting said adsorbent with a fluid desorbent material to effect desorption of said ester of a more unsaturated fatty acid from said solid adsorbent; and
   (d) removing from said solid adsorbent an extract stream enriched (relative to the composition of the original mixture) in said ester of a more unsaturated fatty acid;
   wherein said adsorbent comprises an X or Y zeolite containing at cation exchangeable sites at least one cation selected from the group consisting of metals of Group IA of the Periodic Table of Elements, magnesium, calcium, strontium, barium, silver, gold, zinc, nickel, copper, cadmium and mercury and combinations thereof; wherein said fluid desorbent material consists essentially of a mixture of one or more paraffinic hydrocarbons containing from about 5 to about 12 carbon atoms, and one or more ethers having the formula $$R_1-O-R_2 \quad \text{or} \quad$$ 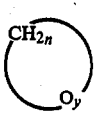

wherein $R_1$ and $R_2$ are alkyl groups containing from about 2 to about 6 carbon atoms, n is 4 or 5, y is 1 or 2 and the sum of n and y is 5 or 6, wherein the volume ratio of paraffinic hydrocarbon to ether is from about 9:1 to 1:9 and wherein contact between solid adsorbent and fluids in said process is effected by means of continuous countercurrent flow fluid-solid contact.

2. The process of claim 1 wherein the feed, desorbent, extract and raffinate streams are all in the liquid state at a temperature range within from about 25° C. to about 300° C. and wherein said process is conducted at a pressure of from about atmospheric pressure to about 500 psig.

3. The process of claim 2 wherein the cations at the cation exchangeable sites of the zeolite adsorbent are selected from the metals of Group IA of the Periodic Table of Elements.

4. The process of claim 3 wherein the mixture of fatty acid esters to be separated comprises an ester of an unsaturated fatty acid and an ester of a saturated fatty acid.

5. The process of claim 4 wherein the ester of the unsaturated fatty acid and the ester of the saturated fatty acid are methyl esters and contain from 14 to 20 carbon atoms in their fatty acid chains.

6. The process of claim 5 wherein the paraffinic hydrocarbon in the desorbent material is acyclic and straight chain and contains from about 5 to about 8 carbon atoms.

7. The process of claim 6 wherein the ether in the desorbent material is a dialkyl ether wherein the alkyl groups are acyclic.

8. The process of claim 7 wherein the ratio of paraffinic hydrocarbon to dialkyl ether in the desorbent material is from about 2:1 to 1:2.

9. The process of claim 8 wherein the paraffinic hydrocarbon is n-hexane and the dialkyl ether is diisopropyl ether.

10. The process of claim 9 wherein the ratio of n-hexane to diisopropyl ether is 1:1.

11. The process of claim 3 wherein the mixture of esters of fatty acids is essentially free of esters of saturated fatty acids.

12. The process of claim 11 wherein the esters of the fatty acids are methyl esters and contain from 14 to 20 carbon atoms in their fatty acid chains.

13. The process of claim 12 wherein the paraffinic hydrocarbon in the desorbent material is acyclic and straight chain and contains from about 5 to about 8 carbon atoms.

14. The process of claim 13 wherein the ether in the desorbent material is a dialkyl ether wherein the alkyl groups are acyclic.

15. The process of claim 14 wherein the ratio of paraffinic hydrocarbon to dialkyl ether in the desorbent material is from about 2:1 to 1:2.

16. The process of claim 15 wherein the paraffinic hydrocarbon is n-hexane and the dialkyl ether is diisopropyl ether.

17. The process of claim 16 wherein the ratio of n-hexane to diisopropyl ether is 1:1.

18. A continuous simulated moving-bed process for the separation of an ester of a more unsaturated fatty acid from a mixture comprising an ester of a more unsaturated fatty acid and an ester of a less unsaturated fatty acid, which process comprises the steps of:
(a) introducing a feed stream of said mixture into a first zone in an adsorption column, which column effects overall fluid flow under substantially isothermal liquid phase conditions from a fourth zone through intervening serially connected third and second ones to a first zone, which column contains at least four serially-connected fixed-beds of an adsorbent, and adsorbing in said first zone at least a portion of said esters of said more unsaturated and less unsaturated fatty acids within the pores of said adsorbent;
(b) in said second zone, located immediately upstream of said first zone, contacting said adsorbent, containing said esters of said more unsaturated and less unsaturated fatty acids within the pores of said adsorbent, with a fluid desorbent material to effect displacement of said ester of a less unsaturated fatty acid from within the pores of said adsorbent;
(c) at the upstream boundary of said second zone, simultaneously withdrawing an extract stream comprising at least a portion of said ester of a more unsaturated fatty acid which has been previously desorbed in said third zone immediately upstream of said second zone;
(d) simultaneously introducing into said third zone, a desorbent material stream to effect said desorption;
(e) at the upstream boundary of said fourth zone located immediately upstream of said third zone and in open fluid communication with said first and said third zones, simultaneously withdrawing a relatively less selectively adsorbed raffinate stream comprising at least a portion of said ester of a less unsaturated fatty acid; and
(f) periodically and simultaneously advancing the points of introduction of said feed stream and said desorbent material, and the points of withdrawal of said extract stream and said raffinate stream, one bed length in a downstream direction;

wherein in said process the adsorbent comprises an X or a Y zeolite containing at exchangeable cationic sites at least one cation selected from the group consisting of cations of metals of Group IA of the Periodic Table of Elements, magnesium, calcium, strontium, barium, silver, gold, zinc, nickel, copper, cadmium and mercury, and combinations thereof, and wherein said desorbent material consists essentially of a mixture of one or more paraffinic hydrocarbons containing from about 5 to about 12 carbon atoms, and one or more ethers having the formula $$R_1-O-R_2 \quad \text{or} \quad$$ 

wherein $R_1$ and $R_2$ are alkyl groups containing from about 2 to about 6 carbon atoms, n is 4 or 5, y is 1 or 2 and the sum of n and y is 5 or 6, and wherein the volume ratio of paraffinic hydrocarbon to ether is from about 1:9 to 9:1.

19. The process of claim 18 wherein the feed, desorbent, extract and raffinate streams are all in the liquid state at a temperature range within from about 25° C. to about 300° C. and wherein said process is conducted at a pressure of from about atmospheric pressure to about 500 psig.

20. The process of claim 19 wherein the cations at the cation exchangeable of Group IA of the Periodic Table of Elements.

21. The process of claim 20 wherein the mixture of fatty acid esters to be separated comprises an ester of an unsaturated fatty acid and an ester of a saturated fatty acid.

22. The process of claim 21 wherein the ester of the unsaturated fatty acid and the ester of the saturated fatty acid are methyl esters and contain from 14 to 20 carbon atoms in their fatty acid chains.

23. The process of claim 22 wherein the paraffinic hydrocarbon in the desorbent material is straight chain and contains from 5 to 8 carbon atoms.

24. The process of claim 23 wherein the ether in the desorbent material is a dialkyl ether wherein the alkyl groups are acyclic.

25. The process of claim 24 wherein the ratio of paraffinic hydrocarbon to dialkyl etherin the desorbent material is from about 2:1 to 1:2.

26. The process of claim 25 wherein the paraffinic hydrocarbon is n-hexane and the dialkyl ether is diisopropyl ether.

27. The process of claim 26 wherein the ratio of n-hexane to diisopropyl ether is 1:1.

28. The process of claims 25, 26 or 27 wherein in the feed stream the esters of unsaturated fatty acids comprise methyl oleate, methyl linoleate, methyl linolenate and mixtures thereof and the esters of saturated fatty acids comprise methyl palmitate, methyl stearate and mixtures thereof.

29. The process of claim 28 wherein the cation at the exchangeable cationic sites in the adsorbent is sodium.

30. The process of claim 20 wherein the mixture of esters of fatty acids is substantially free of esters of saturated fatty acids.

31. The process of claim 30 wherein the esters of the fatty acids are methyl esters and contain from 14 to 20 carbon atoms in their fatty acid chains.

32. The process of claim 31 wherein the paraffinic hydrocarbon in the desorbent material is acyclic and straight chain and contains from about 5 to about 8 carbon atoms.

33. The process of claim 32 wherein the ether in the desorbent material is a dialkyl ether wherein the alkyl groups are acyclic.

34. The process of claim 33 wherein the ratio of paraffinic hydrocarbon to dialkyl ether in the desorbent material is from about 2:1 to 1:2.

35. The process of claim 34 wherein the paraffinic hydrocarbon is n-hexane and the dialkyl ether is diisopropyl ether.

36. The process of claim 35 wherein the ratio of n-hexane to diisopropyl ether is 1:1.

37. The process of claim 34, 35 or 36 wherein in the feed stream the esters of unsaturated fatty acid are selected from the group consisting of methyl oleate, methyl linoleate, methyl linolenate and mixtures thereof.

38. The process of claim 37 wherein the cation at the exchangeable cationic sites iin the adsorbent is sodium

* * * * *

UNITED STATES PATENT AND TRADEMARK OFFICE
CERTIFICATE OF CORRECTION

PATENT NO. : 4,210,594
DATED : July 1, 1980
INVENTOR(S) : Ted J. Logan and David C. Underwood It is certified that error appears in the above-identified patent and that said Letters Patent are hereby corrected as shown below:

Col. 11, Table II, shift entire line for Cycle 8* to the right so as to align 8* under 7.

Col. 11, line 63, "be" should be -- bed --.

Col. 15, line 37, "voia" should be -- void --.

Col. 15, line 60, "selectively" should be -- selectivity --.

Col. 18, line 16, "ones" should be -- zones --.

Col. 19, line 10, after "exchangeable" insert --  sites of the zeolite adsorbent are selected from the metals --.

Col. 19, line 27, "etherin" should be -- ether --.

Col. 20, line 28, "claim" should be -- claims --.

Col. 20, line 34, "iin" should be -- in --.

Signed and Sealed this

Ninth Day of December 1980

[SEAL]

Attest:

SIDNEY A. DIAMOND

Attesting Officer

Commissioner of Patents and Trademarks